(12) United States Patent
Samaniego et al.

(10) Patent No.: US 9,504,557 B1
(45) Date of Patent: Nov. 29, 2016

(54) HIGH-STRENGTH ALLOGRAFT TENDON CONSTRUCT

(71) Applicant: Allosource, Centennial, CO (US)

(72) Inventors: Adrian Samaniego, Centennial, CO (US); Matt Southard, Westminster, CO (US); Wendy Desiree Franklin, Westminster, CO (US); Jessica Hodgkiss, Denver, CO (US); Bilal Karaze, Aurora, CO (US)

(73) Assignee: Allosource, Centennial, CO (US)

( * ) Notice: Subject to any disclaimer, the term of this patent is extended or adjusted under 35 U.S.C. 154(b) by 0 days.

(21) Appl. No.: 15/073,582

(22) Filed: Mar. 17, 2016

(51) Int. Cl.
*A61F 2/08* (2006.01)

(52) U.S. Cl.
CPC ............... *A61F 2/08* (2013.01); *A61F 2/0811* (2013.01); *A61F 2002/087* (2013.01)

(58) Field of Classification Search
CPC .................................. A61F 2/08; A61F 2/0811
See application file for complete search history.

(56) References Cited

U.S. PATENT DOCUMENTS

| | | | |
|---|---|---|---|
| 5,197,983 | A | 3/1993 | Berman et al. |
| 5,800,543 | A | 9/1998 | McLeod et al. |
| 8,202,318 | B2 | 6/2012 | Willobee |
| 8,298,284 | B2 | 10/2012 | Cassani |
| 2001/0018619 | A1* | 8/2001 | Enzerink .................. A61F 2/08 623/23.72 |
| 2002/0165611 | A1 | 11/2002 | Enzerink et al. |
| 2007/0118217 | A1 | 5/2007 | Brulez et al. |
| 2008/0027485 | A1 | 1/2008 | Jolly et al. |
| 2009/0318958 | A1 | 12/2009 | Ochiai |
| 2012/0253465 | A1* | 10/2012 | Missos ..................... A61F 2/08 623/13.19 |
| 2013/0023927 | A1 | 1/2013 | Cassani |
| 2016/0008123 | A1 | 1/2016 | Woodruff et al. |

OTHER PUBLICATIONS

International Search Report and Written Opinion for international application No. PCT/US16/22984 dated May 31, 2016, 6 pp.

* cited by examiner

*Primary Examiner* — David Isabella
*Assistant Examiner* — Suba Ganesan
(74) *Attorney, Agent, or Firm* — James A. Sheridan; Sheridan Law, LLC

(57) ABSTRACT

There is disclosed an apparatus and method of manufacture relating to a pre-sutured, high-strength allograft tendon construct. One embodiment of the allograft tendon construct includes first and second tendon lengths that are positioned longitudinally in parallel to one another. A whip stitched pattern secures the first and second tendon lengths at a free end, forming a stitched end portion that abuts an unstitched middle portion. The whip stitched pattern includes a plurality of sutures that originate adjacent to the free end and progress or advance inward toward the unstitched middle portion. A multiple knot bundle is applied immediately prior to a final suture, such that the final suture loops about the multiple knot bundle and locks the multiple knot bundle in place beneath the final suture. Other embodiments are also disclosed.

18 Claims, 12 Drawing Sheets

HIGH-STRENGTH ALLOGRAFT TENDON CONSTRUCT

BACKGROUND

An allograft includes bone, tendon, skin, or other types of tissue transplanted from one person to another. Allografts are used in a variety of medical treatments, such as knee replacements, bone grafts, spinal fusions, eye surgery, and skin grafts for the severely burned. Allografts come from voluntarily donated human tissue obtained from donor-derived, living-related, or living-unrelated donors and can help patients regain mobility, restore function, enjoy a better quality of life, and even save lives.

When a ligament or tendon becomes detached from the bone, surgery is usually required to re-secure the ligament or tendon. Often, a substitute allograft ligament or tendon (hereinafter an "allograft construct" or "allograft tendon construct") is attached to the bone to facilitate regrowth and permanent attachment. The reattachment procedure involves drilling a bone tunnel between two bones such as, for example, the tibia and the femur, and securing the allograft construct within the tunnel. To demonstrate this technique, Prior Art FIG. 1 shows an exemplary prior art allograft construct 50 secured within femoral and tibial tunnels 52, 54, each formed in femur and tibia 56, 58, respectively.

An allograft construct must be properly tensioned within the bone tunnel to achieve optimal results. That is, the tension or the "fit" of the allograft construct within the bone tunnel prior to being anchored to the bone must be sufficient to achieve stability, but not so excessive that it captures the joint. One variable in achieving optimal tension of the allograft construct within the bone tunnel involves preparing an allograft construct having the proper cross-sectional diameter. Preparing a construct with the requisite cross-sectional diameter typically involves folding a single tendon strand in half, which results two abutting tendon lengths having in a common middle region bounded by a folded end and a free end. The free end may then be whip stitched together. Alternatively, two separate tendon strands may be associated with one another, or "doubled up," before one or both free ends are whip stitched together.

Prior Art FIG. 2 illustrates a partial perspective view of an unstitched middle region 59 and a free end 60 of prior art allograft construct 50, in which free end 60 has been whip stitched using a flexible strand to form a stitched pattern 62. Notably, the whip stitched pattern 62 of prior art allograft construct 50 originates inward toward unstitched middle region 59, from where a number of sutures $64_{1-5}$ progress or advance outward toward free end 60 along arrow A. As a result, final suture $64_5$ is located adjacent to free end 60, and pulling forces applied to the flexible strand along arrow B are transferred to final suture $64_5$ at free end 60.

Prior art stitch pattern 62 is often applied to a folded allograft tendon, and discussed above. Alternatively, it is applied to two independent tendon strands that are stitched together at one or both of their ends using a similar whip stitching technique.

Traditionally, surgeons have been responsible for tendon graft preparation, individually preparing appropriately cross-sectioned, whip stitched grafts for each patient and/or circumstance. Recently, pre-sutured allograft constructs have become available from third-part providers, such as, for example, allograft processing centers, thereby allowing surgeons to order high quality, consistent, strong, and sterile tendon allografts, either individually or as part of a larger "kit" carrying a variety of sizes.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a method of tendon reconstruction. The method includes (1) positioning a first tendon length and a second tendon length longitudinally in parallel to one another; (2) threading a flexible strand through and about a first free end of the first and second tendon lengths to form an allograft construct having a stitched end portion that abuts an unstitched middle portion, where the threading comprises forming a plurality of sutures by advancing the flexible strand away from a first suture located adjacent to the first free end and toward a final suture located adjacent to the unstitched middle portion; and (3) after forming the final suture, stringing the flexible strand through a space between the first and second tendon lengths and out the first free end of the stitched end portion.

Another embodiment provides an allograft construct. The allograft construct includes a first tendon length and a second tendon length, where the first and second tendon lengths are positioned longitudinally in parallel to one another. The allograft construct also includes a whip stitched pattern that secures together the first and second tendon lengths at a fee end, thereby forming a stitched end portion that abuts an unstitched middle portion. The whip stitched pattern includes a plurality of sutures that originate adjacent to the free end and progress inward toward the unstitched middle portion.

Yet another embodiment provides a substitute tendon having at least a stitched end portion and an unstitched middle portion and including a continuous flexible strand forming a whip stitched pattern and an anchor. The whip stitched pattern comprises a plurality of sutures that secure a common free end of two longitudinally abutting tendon lengths, the plurality of sutures originating with a first suture located adjacent to the free end and progressing toward a final suture located adjacent to the unstitched middle portion. The anchor originates at the final suture and threads through a space between the tendon lengths and out the common free end of the stitched end portion.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to a pre-sutured, high-strength allograft construct that may be pre-ordered and made available for a surgeon to position and affix in place within a target bone tunnel(s) of a patient. The allograft construct features a whip stitched suture pattern that outperforms current methods of suturing tendons and ligaments for use in tendon replacement surgeries (e.g., ACL replacement surgeries). One embodiment provides an allograft tendon construct having a whip stitched suture pattern that originates at an outermost end of the allograft construct and progresses inward. The new suture pattern results in a stronger final product that increases the maximum force that can be applied to a pre-sutured tendon construct without risking suture pull-out and/or slippage. This unique pattern also prevents deformation of the allograft tendon construct when subjected to the type of excessive tensile forces that are often applied to the suture pattern after surgery and in use.

Figure 3:
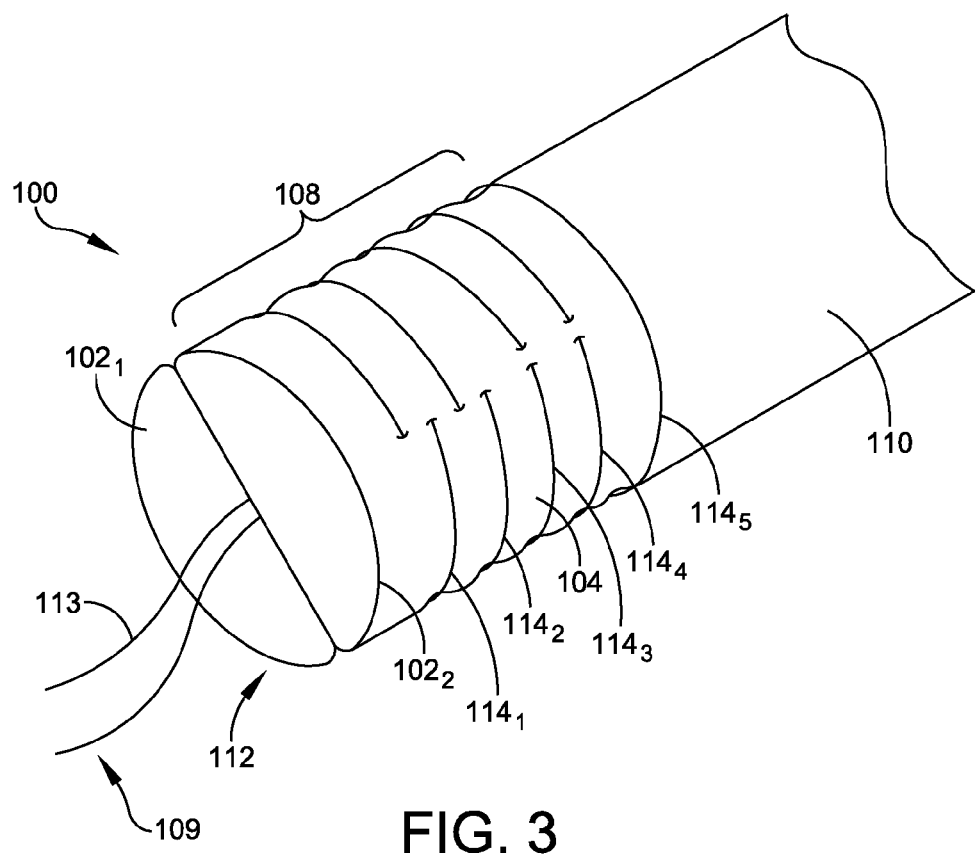
FIG. 3 illustrates a partial-perspective view of one embodiment of a high-strength, pre-sutured allograft tendon construct.

FIG. 3 illustrates a partial perspective view of one embodiment of a high-strength allograft construct 100. In this embodiment, allograft construct 100 may include first and second tendon lengths $102_1$, $102_2$ that have been whip stitched together at a stitched end portion 104. Stitched end portion 104 may secure a common free end 112 with a whip stitched pattern 108, which, in this embodiment, may include five sutures $114_{1-5}$, and an anchor 109. Stitched end portion 104 may abut an unstitched middle portion 110.

Whip stitched pattern 108 may be needle-threaded through and about first and second tendon lengths $102_1$, $102_2$. Pattern 108 and anchor 109 may be formed of any appropriate and continuous flexible strand 113, including suture material of rope or wire that is formed of natural or manmade materials that do not react negatively with human tissue.

FIGS. 4-13 detail the intricacies of whip stitched pattern 108 and anchor 109 to demonstrate how high-strength allograft construct 100 resists maximum pull-out force, while also resisting suture deformation and slippage. Specifically, FIGS. 4A-4C illustrate side-partial, end, and perspective-partial views of first tendon length $102_1$ and second tendon length $102_2$ positioned in parallel along a longitudinal axis, X. Each of first and second tendon lengths $102_1$, $102_2$ may be formed of separate tendon or ligament strands. Alternatively, and as shown in FIG. 4D, first and second tendon lengths $102_1$, $102_2$ may be formed of first and second halves of a single tendon or ligament strand that has been folded over or doubled. In either alternative, first and second tendon lengths $102_1$, $102_2$ may meet at a common free end 112 (FIGS. 4B-4C).

Figure 5A:
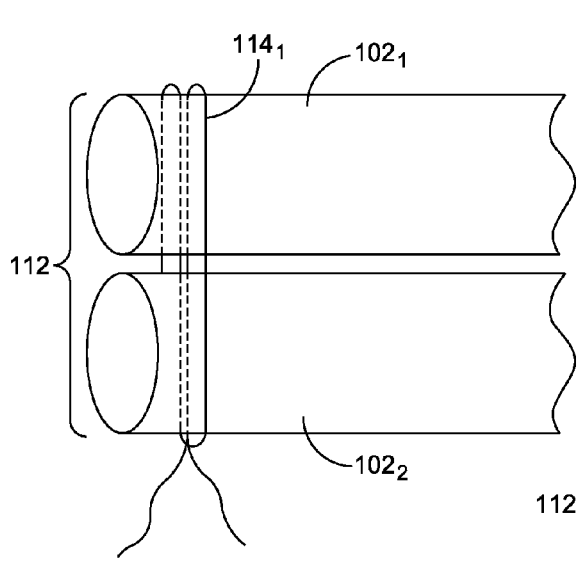
FIGS. 5A-5C illustrate respective partial-side, end, and partial-perspective views of the first and second tendon lengths of FIGS. 4A-4C, including a first suture applied adjacent to a free end.
Figure 5B:
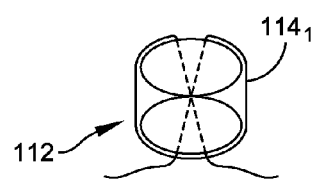
Figure 5C:
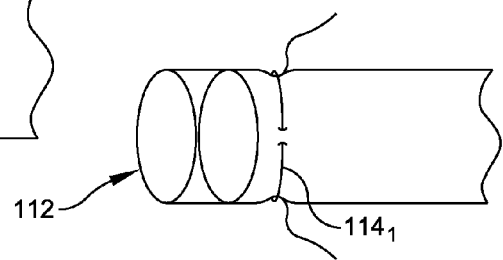
Figure 6A:
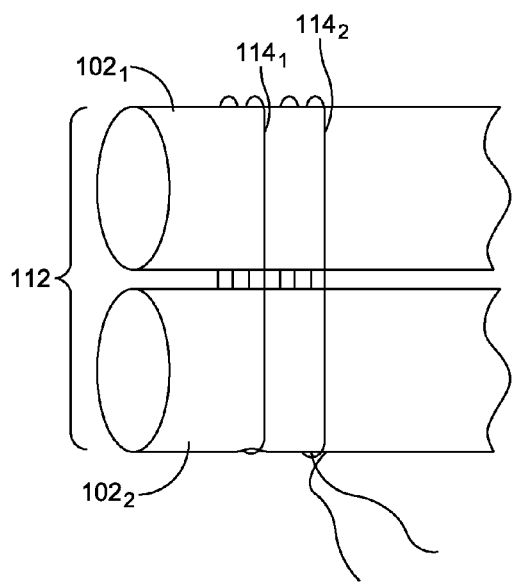
FIGS. 6A-6C illustrate respective partial-side, end, and partial-perspective views of the first and second tendon lengths of FIGS. 4A-4C, including a first suture located adjacent to a free end and a second suture applied in a direction progressing inward toward an unstitched middle portion.
Figure 6B:
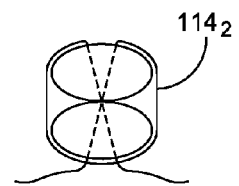
Figure 6C:
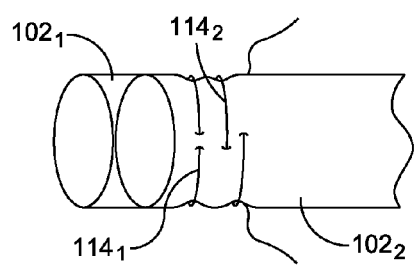

FIGS. 5A-5C and 6A-6C illustrate side-partial, end, and perspective-partial views of first and second sutures $114_1$, $114_2$, respectively, as applied to free end 112 of first and second tendon lengths $102_1$, $102_2$. As shown in FIGS. 5A-5C, first suture $114_1$ threads flexible strand 113 both through and about free end 112, securing both tendon lengths $102_1$, $102_2$ relative to one another. Second suture $114_2$, added in FIGS. 6A-6C, repeats the loop. Notably, first suture $114_1$ originates at a location adjacent to free end 112. As a result, additional sutures $114_{2-n}$ progress or advance inward toward unstitched middle portion 110 (FIG. 3).

Figure 7A:
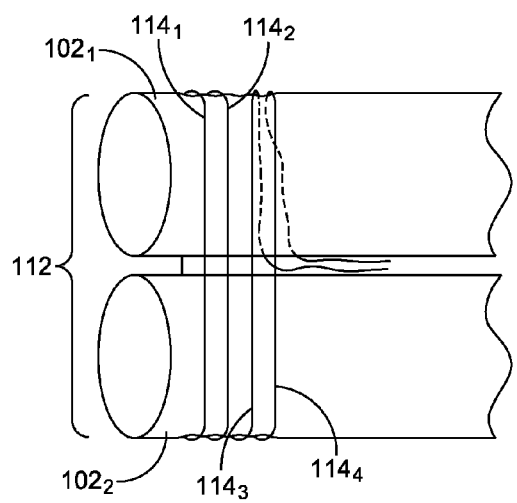
FIGS. 7A-7C illustrate respective partial-side, end, and partial-perspective views of the first and second tendon lengths of FIGS. 4A-4C, including first through fourth sutures that originate adjacent to a free end and progress inward toward an unstitched middle portion.
Figure 7B:
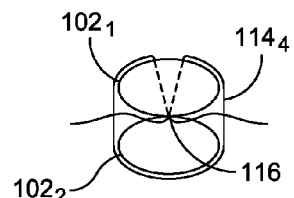
Figure 7C:
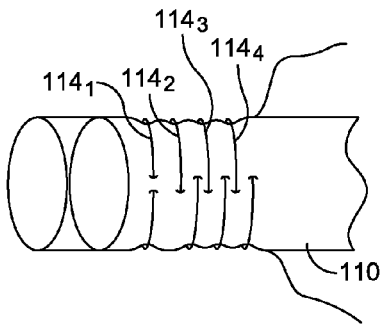
Figure 8A:
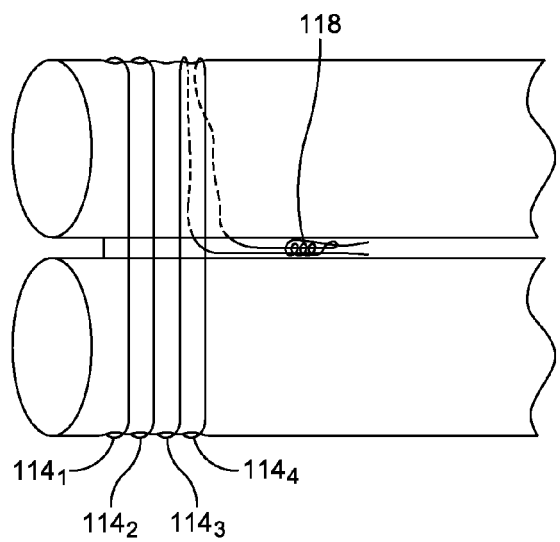
FIGS. 8A-8C illustrate respective partial-side, end, and partial-perspective views of the first and second tendon lengths and sutures of FIGS. 7A-7C, including a Duncan Loop knot applied after the fourth suture.
Figure 8B:
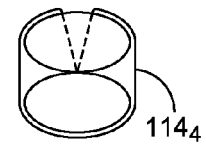
Figure 8C:
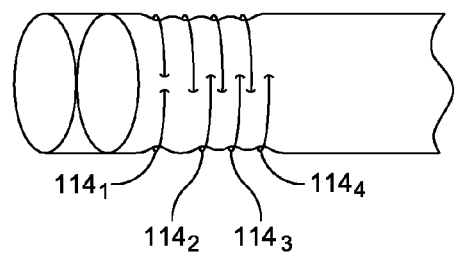
Figure 9:
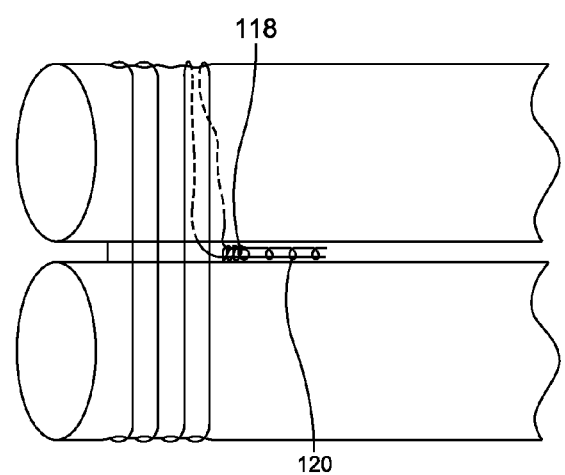
FIG. 9 illustrates a partial-side view of the first and second tendon lengths, sutures, and Duncan loop knot of FIGS. 8A-8C, including three Reverse-Half-Hitch-Alternating-Post knots applied after the Duncan loop knot.
Figure 10:
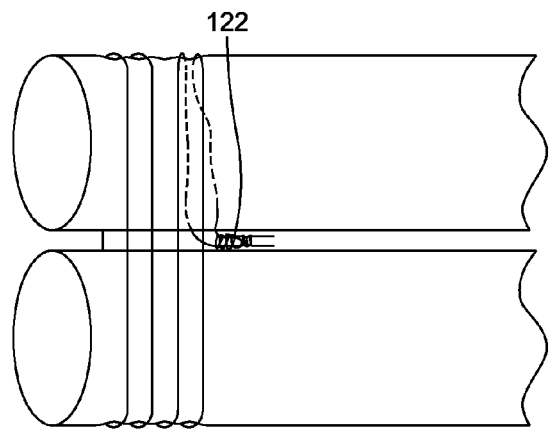
FIG. 10 illustrates a partial-side view of the first and second tendon lengths, sutures, and knots of FIG. 9, where the knots are tightened into a multiple knot bundle.
Figure 11A:
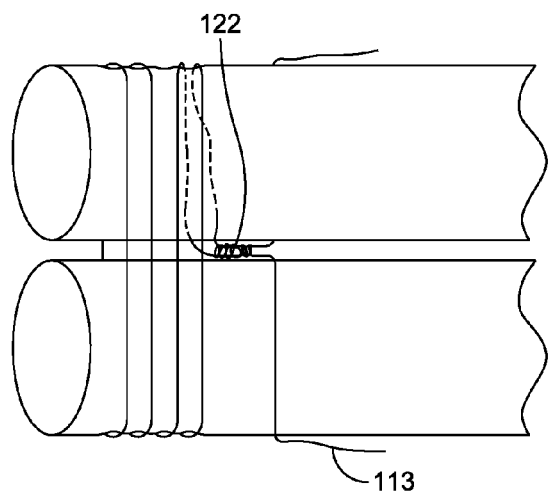
FIGS. 11A-11C illustrate respective partial-side, end, and partial-perspective views of the first and second tendon lengths, sutures, and multiple knot bundle of FIG. 10, including an initiated fifth suture.
Figure 11B:
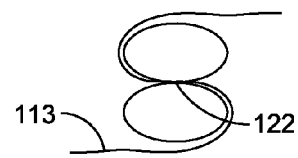
Figure 11C:
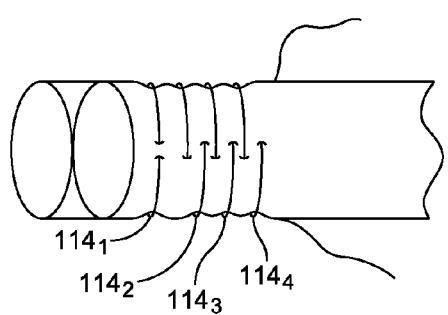
Figure 12A:
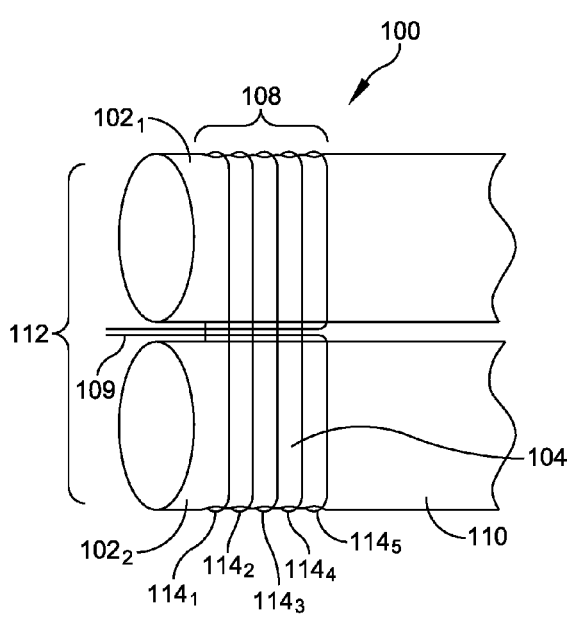
FIGS. 12A-12C illustrate respective partial-side, end, and partial-perspective views of the first and second tendon lengths, sutures, and multiple knot bundle of FIGS. 11A-11C, with an anchor threaded through a space between the tendon lengths and out a free end.
Figure 12B:
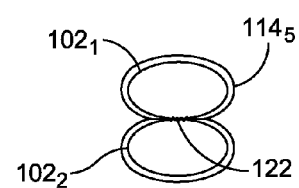
Figure 12C:
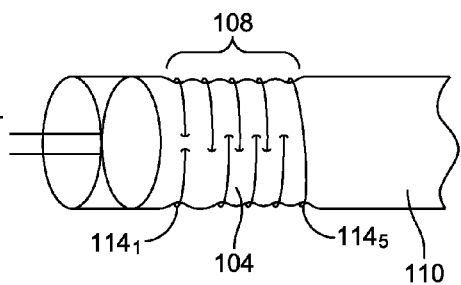

FIGS. 7A-7C illustrate side-partial, end, and perspective-partial views of first through fourth sutures $114_{1-4}$, as applied to free end 112 of first and second tendon lengths $102_1$, $102_2$. In this embodiment, fourth suture $114_4$ is the fourth of five total sutures $114_{1-5}$. That is, suture $114_4$ is the second-to-last suture, and, therefore, suture $114_4$ may differ slightly from sutures $114_{1-3}$ in that flexible strand 113 may exit the loop prior to completion at a space or junction 116 between first and second tendon lengths $102_1$, $102_2$, as shown in FIG. 7B. Once flexible strand 113 has exited suture $114_4$, a Duncan loop Knot 118 may be applied, as shown in FIGS. 8A-8C, and tightened. In this embodiment, Duncan loop Knot 118 may be followed by three Reverse-Alternating-Post-Half- Hitch knots 120, shown in FIG. 9. Duncan Loop Knot 118, along with Reverse-Alternating-Post-Half-Hitch knots 120 may then be tightened to form a multiple knot bundle 122, shown in FIG. 10.

FIGS. 11A-11C and 12A-12C illustrate side-partial, end, and perspective-partial views of an initiation and completion of fifth and final suture $114_5$, respectively. As shown in FIGS. 11A-11C and 12A-12C, final suture $114_5$ may loop about first and second tendon lengths $102_1$, $102_2$ in a manner that locks-in multiple knot bundle 122, or that secures multiple knot bundle 122 beneath the flexible strand 113 of final suture $114_5$. This configuration ensures that multiple knot bundle 122 is protected or safeguarded beneath the suture that experiences the highest pull-out forces during use, or beneath final suture $114_5$. As force is applied, final suture $114_5$ cinches about multiple knot bundle 122 and tendon lengths $102_1$, $102_2$, which further stabilizes multiple knot bundle 122 to resist pull-out of the knots.

The completion of final suture $114_5$ completes whip stitched pattern 108. Any trailing flexible strand 113 may, in this embodiment, form anchor 109 that is strung or threaded back through the center space 116 between first and second tendon lengths $102_1$, $102_2$ and out free end 112 of stitched end portion 104. Anchor 109 may then be used to anchor or affix allograft construct 100 within a target bone tunnel (not shown) of a patient.

Figure 13:
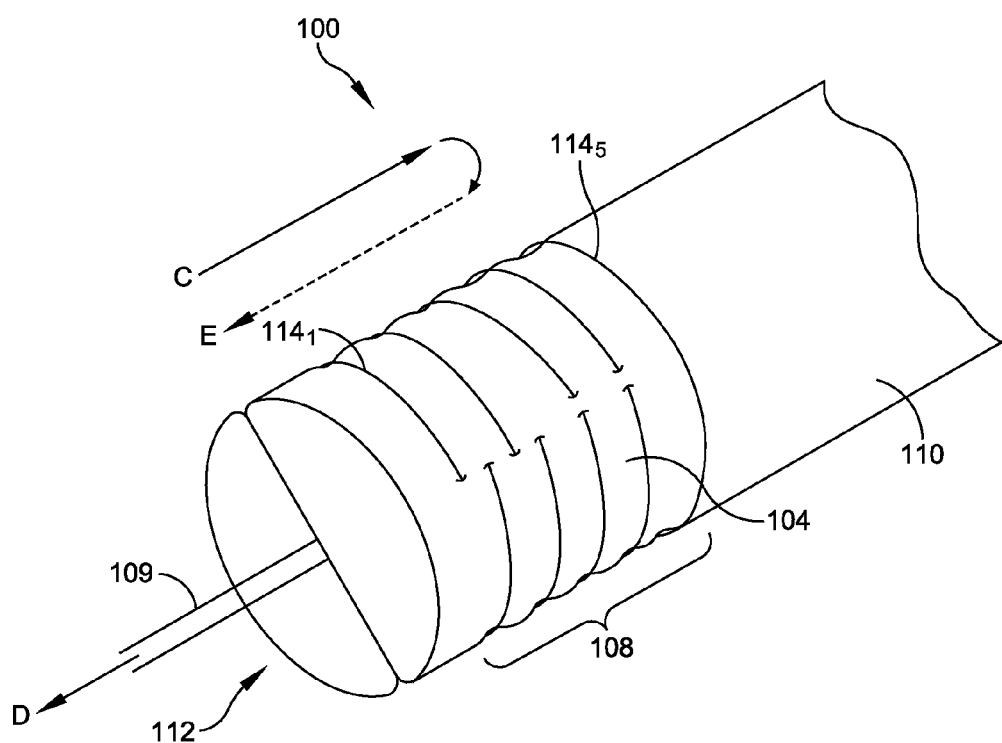
FIG. 13 illustrates a partial-perspective view of the high-strength, pre-sutured allograft tendon construct of FIG. 3, including indications of a direction of suture progression and directions of force application and force transfer.

FIG. 13 illustrates a partial perspective view of completed allograft construct 100, featuring the whip stitched pattern 108. In this embodiment, as discussed above, first suture $114_1$ is located adjacent to free end 112. The remaining sutures $114_{2-5}$ progress inward along arrow C toward unstitched middle section 110, such that final suture $114_5$ is placed at the farthest point from free end 112. As a result, tensile force applied to anchor 109 along arrow D is transferred directly to final suture $114_5$ at the innermost area of stitched end 104, causing final suture $114_5$ to cinch/lock about tendon lengths $102_1$, $102_2$ upon the application of force. Excess force is then translated to the previous suture, or fourth suture $114_4$, then to suture $114_3$, then to suture $114_2$, and finally to suture $114_1$, causing whip stitched pattern 108 to tighten along arrow E like a noose when under stress.

Figure 1:
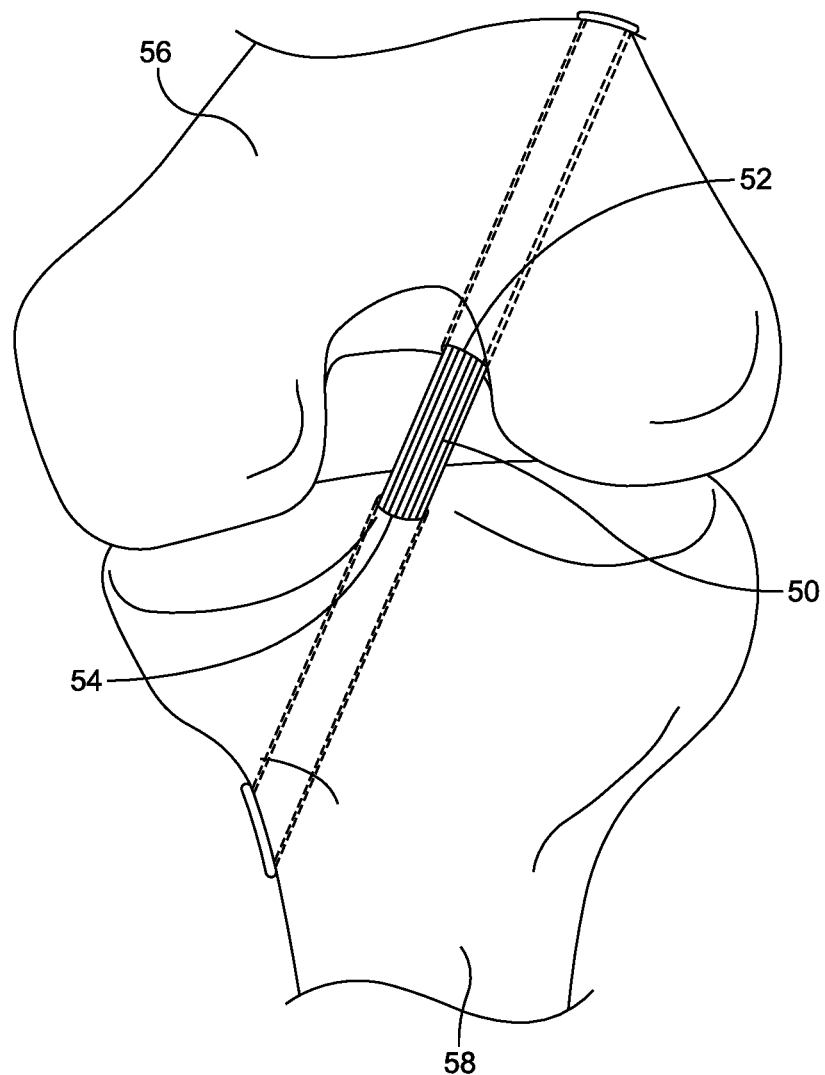
FIG. 1 illustrates a perspective view of a prior art allograft construct affixed within femoral and tibial bone tunnels of a patient.
Figure 2:
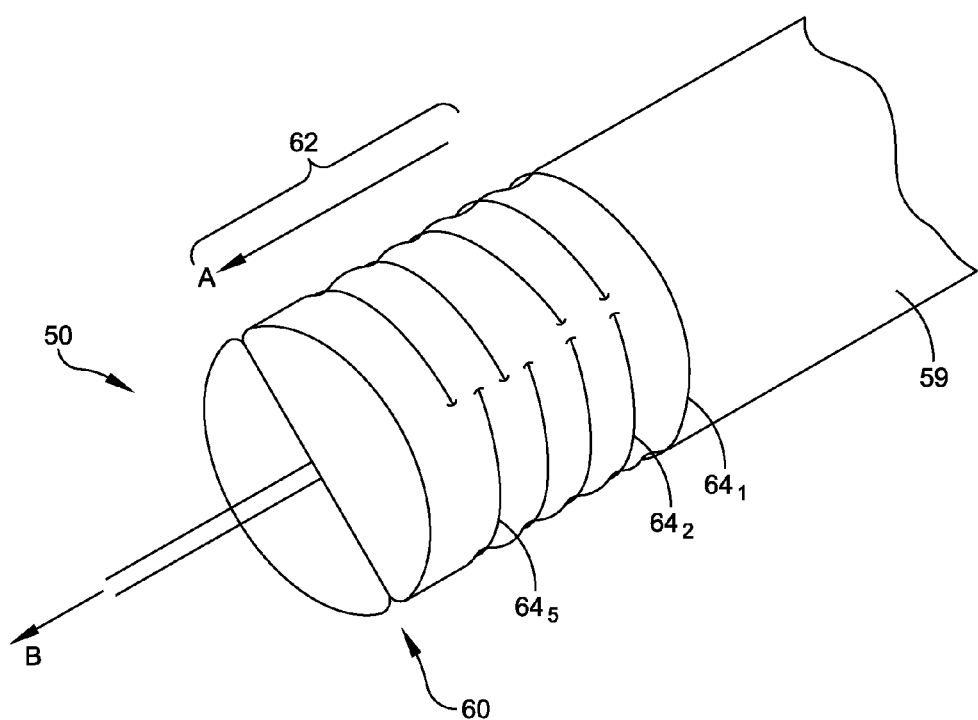
FIG. 2 illustrates a partial-perspective view of the prior art allograft construct of FIG. 1.

In use, the highest force is always experienced by final suture $114_5$, which is farthest from the edge of construct 100. The least amount of force is transferred to the most vulnerable first suture $114_1$, located closest to the edge of construct 100. This configuration allows allograft construct 100 with whip stitched pattern 108 to resist much higher applied forces than prior art constructs (e.g., prior art construct 50 of FIG. 2) without experiencing suture pull-out and/or deformation because far more tendon material separates the most highly stressed suture from the edge of the construct.

As discussed above in the Background section, prior art whip stitched patterns typically place the first suture at an inward location toward the unstitched middle portion of the construct and progress the remaining sutures outward toward the open end/edge of the construct. As a result, the final suture in the prior art commonly resides adjacent to the free end. Thus, the highest force applied to the prior art anchor is transferred directly to the final suture, located closest to the end of the construct, which often results in suture pull-out and/or deformation.

Allograft construct 100 also serves to prevent knot pull-out because multiple knot bundle 122 (FIGS. 10 and 11A) is applied immediately prior to the final suture, or between the second-to-final suture (here, fourth suture $114_4$) and the final suture (here, final suture $114_5$). This positioning allows the final suture to "lock-in" the multiple knot bundle, or to tighten about the multiple knot bundle upon the application of force, thereby preventing knot pull-out.

Plane strain tensile (PST) testing was performed on six sample allograft constructs, including three prior art constructs (labeled "Old" or "O") and three constructs featuring whip stitched pattern 108 (labeled "New" or "N"). The results are shown in Table 1, below.

TABLE 1

| | Deformation of Construct >1 cm or Suture Failure | | |
|---|---|---|---|
| Sample | Deformation of >1 cm (lbs) | Suture yield (lbs) | Whip Stitch Suture Technique Old OR New |
| A | na | 64.5 | N |
| B | 6.8 | na | O |
| C | na | 63.4 | N |
| D | na | 67.3 | N |
| E | 5.6 | na | O |
| F | 4.5 | na | O |

Testing criteria was set to "fail" at the point where elongation of the construct exceeded 1 cm. The force required to reach the point of failure, as well as the force at which the suture failed, were recorded to demonstrate the integrity of each suture. As shown in Table 1, none of the prior art samples maintained tissue integrity until suture yield (i.e., the construct deformed beyond 1 cm or the sutures pulled out prior to the point of suture breakage), while all of the constructs featuring stitched pattern 108 maintained tissue integrity until the suture broke at its expected value above 60 pounds of force. Constructs featuring stitching pattern 108 experienced no deformation throughout the tensile strength of the suture, while all of the prior art constructs experienced deformation of the construct beyond the allowable 1 cm and did not exhibit tensile strength beyond 6.8 lbs.

Figure 4A:
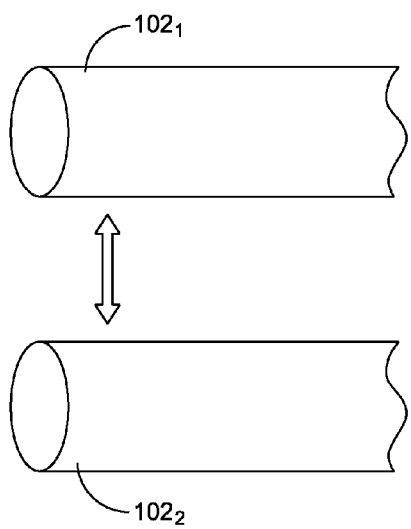
FIGS. 4A-4C illustrate respective partial-side, end, and partial-perspective views of first and second tendon lengths of the allograft construct of FIG. 3.
Figure 4B:
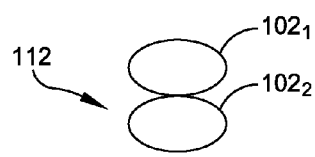
Figure 4C:
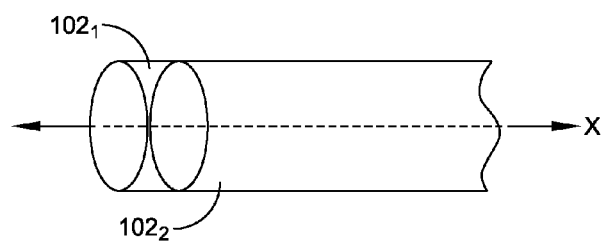
Figure 4D:
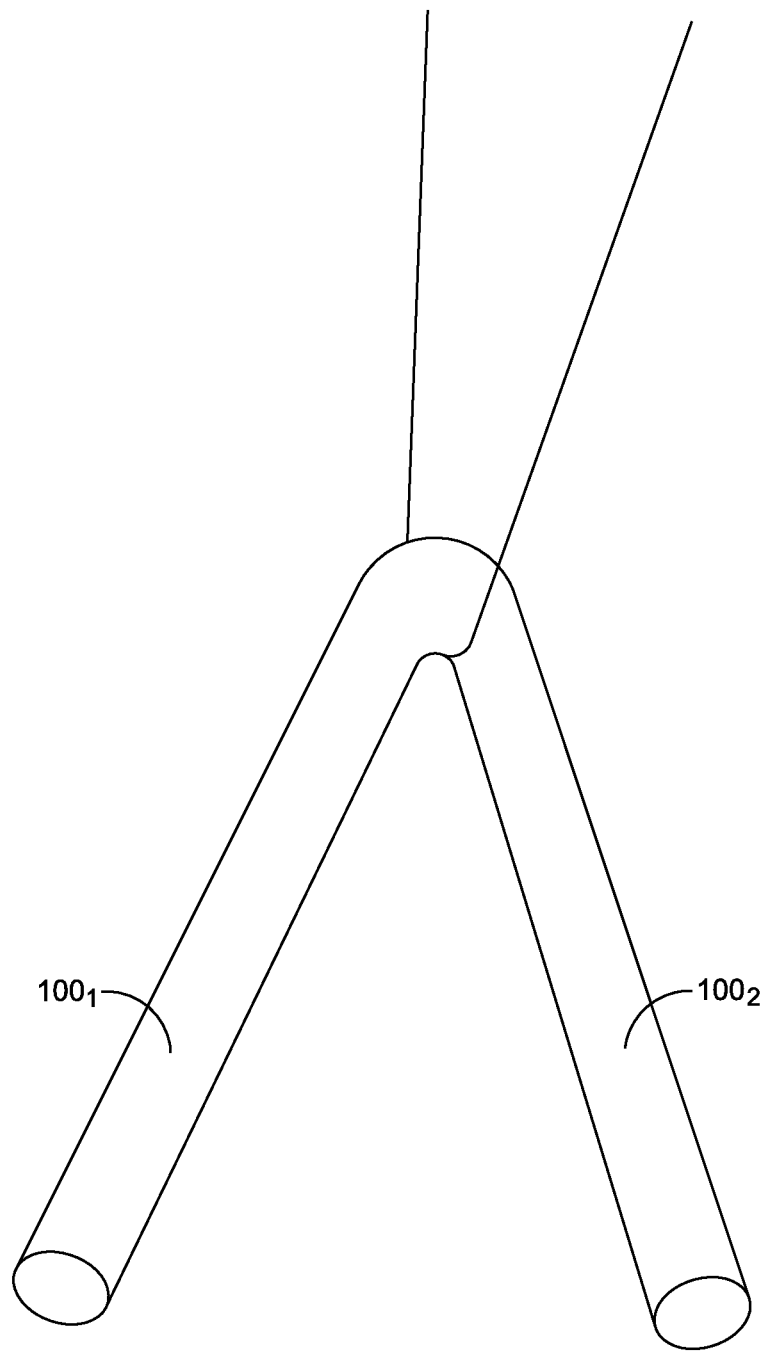
FIG. 4D illustrates a perspective view of one embodiment of a folded-over tendon strand forming the first and second tendon lengths of FIGS. 4A-4C.
Figure 14:
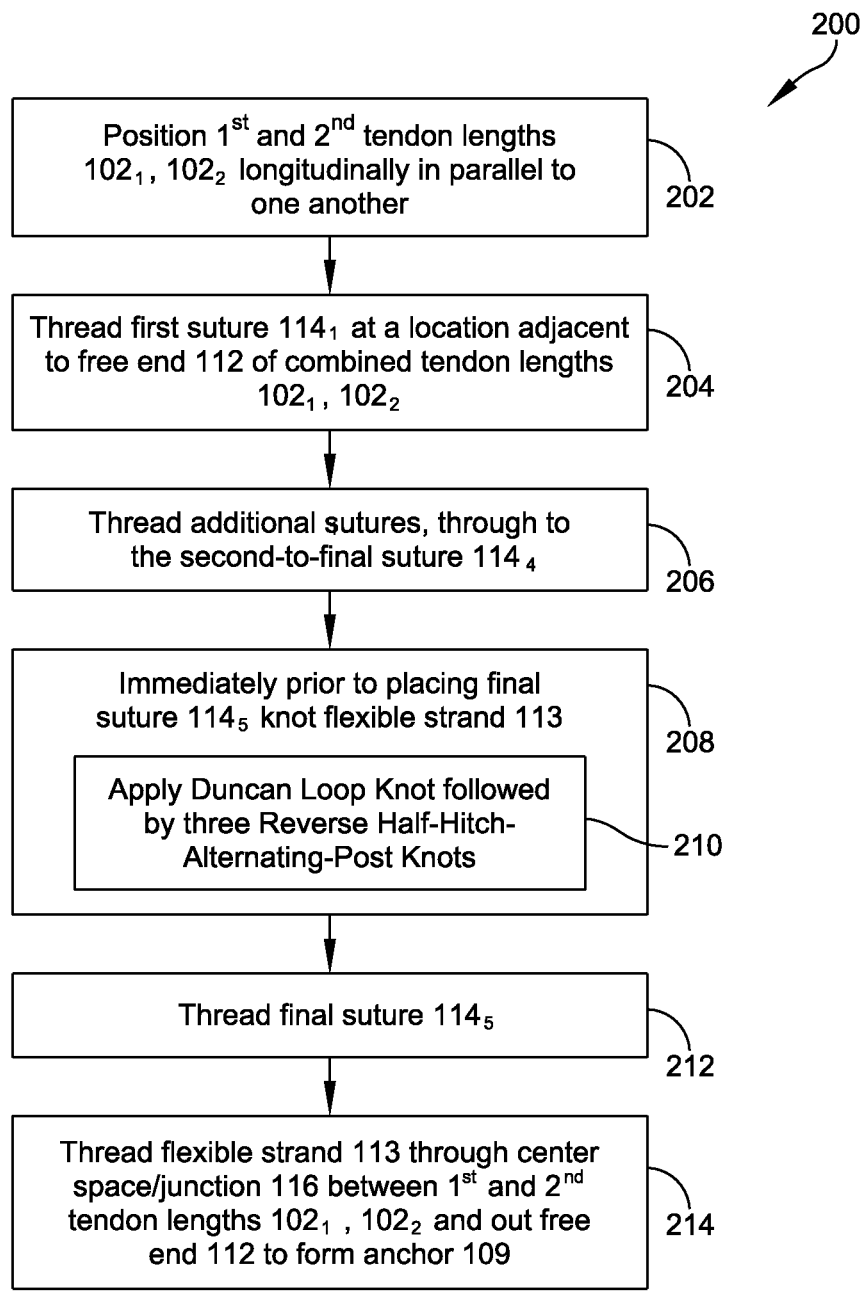
FIG. 14 illustrates a flow chart depicting an exemplary method of manufacturing the high-strength, pre-sutured allograft tendon construct of FIG. 13.

FIG. 14 provides a flow chart illustrating an exemplary method 200 of manufacturing one embodiment of high-strength allograft construct 100. Method 200 initiates with the positioning (202) of first tendon length $102_1$ and second tendon length $102_2$ longitudinally in parallel to one another. As discussed above, this positioning may include placing independent tendon strands side-by-side or by folding over a single tendon strand to form two distinct lengths $102_1$, $102_2$, as shown in FIG. 4D. Method 200 continues with the threading (204) of flexible strand 113 through and about free end 112 to form first suture $114_1$ located adjacent to free end 112 of combined tendon lengths $102_1$, $102_2$. After the placement of first suture $114_1$, method 200 may continue with the threading of additional sutures (206), such as sutures $114_{2-4}$, which progress inward toward unstitched middle portion 110. Additional sutures may be threaded through to the second-to-final suture, or, in this embodiment, fourth suture $114_4$. After placing the second-to-final suture and immediately prior to placing the final suture, flexible strand 113 may be knotted (208). In one embodiment, knotting flexible strand 113 (208) may involve applying a Duncan Loop Knot 118, followed by three Reverse Half-Hitch-Alternating-Post Knots 120 (210) to form multiple knot bundle 122. After knotting (208) flexible strand 113, method 200 may continue with the threading of a final suture (212) (e.g., final suture $114_5$) to complete whip stitched pattern 108. Final suture $114_5$ may be looped about multiple knot bundle 122 to guard against knot pull-out, as discussed above. Once the final knot has been applied (212), flexible strand 113 may be threaded through center space/junction 116 between first and second tendon lengths 102₁, 102₂ and out free end 112 to form anchor 109 (214), which may be affixed within a target bone tunnel of a patient.

While method 200 discusses whip stitched pattern as having a total of five suture, it should be understood that any appropriate number of sutures may apply.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of tendon reconstruction, comprising:
    positioning a first tendon length and a second tendon length longitudinally in parallel to one another;
    threading a flexible strand through and about a first free end of the first and second tendon lengths to form an allograft construct having a stitched end portion that abuts an unstitched middle portion, wherein the threading comprises forming a plurality of sutures by advancing the flexible strand away from a first suture located adjacent to the first free end and toward a final suture located adjacent to the unstitched middle portion; and
    after forming the final suture, stringing the flexible strand through a center space between the first and second tendon lengths and out the first free end of the stitched end portion.

2. The method of claim 1, further comprising knotting the flexible strand immediately prior to forming the final suture.

3. The method of claim 2, wherein the knotting comprises applying a multiple knot bundle.

4. The method of claim 3, wherein the multiple knot bundle comprises a Duncan-Loop knot followed by three Reverse-Alternating-Post-Half-Hitch knots.

5. The method of claim 3, wherein the forming of the final suture comprises looping the flexible strand about the multiple knot bundle such that the final suture locks-in the multiple knot bundle.

6. The method of claim 1, further comprising anchoring the flexible strand to a target bone tunnel such that tensile force applied to the flexible strand is transferred to the final suture located adjacent to the unstitched middle portion of the allograft construct.

7. The method of claim 1, wherein first and second halves of a folded over tendon strand form the first and second tendon lengths, respectively.

8. An allograft construct, comprising:
    a first tendon length and a second tendon length, the first and second tendon lengths positioned longitudinally in parallel to one another; and
    a whip stitched pattern securing together the first and second tendon lengths at a free end, thereby forming a stitched end portion that abuts an unstitched middle portion, the whip stitched pattern comprising a plurality of sutures that originate adjacent to the free end and progress toward the unstitched middle portion;
    wherein the plurality of sutures comprises at least a first suture located at the free end and a final suture located adjacent to the unstitched middle portion; and
    an anchor that originates at the final suture and threads through a center space between the first and second tendon lengths and out the free end of the stitched end portion.

9. The allograft construct of claim 8, wherein a continuous flexible strand forms the whip stitched pattern and the anchor.

10. The allograft construct of claim 9, wherein the flexible strand forms a multiple knot bundle immediately prior to the final suture.

11. The allograft construct of claim 10, wherein the multiple knot bundle comprises a Duncan-Loop knot and three Reverse-Alternating-Post-Half-Hitch knots.

12. The allograft construct of claim 10, wherein the final suture loops about the multiple knot bundle such that the final suture locks-in the multiple knot bundle.

13. The allograft construct of claim 8, wherein first and second halves of a folded over tendon strand form the first and second tendon lengths, respectively.

14. A substitute tendon having at least a stitched end portion and an unstitched middle portion, comprising:
    a continuous flexible strand forming a whip stitched pattern and an anchor, wherein:
    the whip stitched pattern comprises a plurality of sutures that secure a common free end of two longitudinally abutting tendon lengths, the plurality of sutures originating with a first suture located adjacent to the free end and progressing toward a final suture located adjacent to the unstitched middle portion; and
    the anchor originates at the final suture and threads through a center space between the tendon lengths and out the common free end of the stitched end portion.

15. The substitute tendon of claim 14, wherein the continuous flexible strand forms a multiple knot bundle immediately prior to the final suture.

16. The substitute tendon of claim 15, wherein the multiple knot bundle comprises a Duncan-Loop knot and three Reverse-Alternating-Post-Half-Hitch knots.

17. The substitute tendon of claim 15, wherein the final suture loops about the multiple knot bundle such that the final suture locks-in the multiple knot bundle.

18. The substitute tendon of claim 14, wherein when tensile force is applied to the anchor, the force is first transferred to the final suture located adjacent to the unstitched middle portion before progressively transferring outward through the whip stitched pattern until reaching the first suture located adjacent to the free end, thereby causing an entirety of the whip stitched pattern to cinch about the two longitudinally abutting tendon lengths.

* * * * *